United States Patent [19]

Harris et al.

[11] Patent Number: 4,897,345
[45] Date of Patent: Jan. 30, 1990

[54] POLLEN TUBE GROWTH ASSAY

[75] Inventors: Philip J. Harris, Auckland, New Zealand; Marilyn A. Anderson, Sunbury; Adrienne E. Clarke, Parkville, both of Australia

[73] Assignee: Lubrizol Genetics Inc., Wickliffe, Ohio

[21] Appl. No.: 75,098

[22] Filed: Jul. 20, 1987

[51] Int. Cl.$^4$ .................... G01N 33/00; G01N 33/554
[52] U.S. Cl. ........................................ 435/7; 436/519; 436/548; 436/811
[58] Field of Search .................... 435/7; 436/519, 548, 436/811

[56] References Cited

U.S. PATENT DOCUMENTS 4,528,267 7/1985 Calenoff et al. ................. 436/532 X

OTHER PUBLICATIONS

Pettitt, J. M., "Ultrastructural . . . Pollen Tube Wall . . .", Chemical Abstracts 98, p. 404, #31522z, Jan. 31, 1983.
Smith, G. A. and Moser H. S. (1985), Theor. Appl. Genet. 71:231–237.
Feder, W. A. (1986) in *Biotechnology and Ecology of Pollen*, (D. L. Mulcahy, G. D. Mulcahy, E. Ottaviano (eds.), Springer-Verlag, New York, pp. 89–94.
Searcy, K. B. and Mulcahy, D. L. (1985) Amer. J. Bot. 72:1700–1706.
Searcy, K. B. & Mulcahy, D. L. (1986) in *Biotechnology and Ecology of Pollen*, (D. L. Mulcahy, G. D. Mulcahy, E. Ottaviano (eds.) Springer-Verlag, N.Y., pp. 159–164.
Shivanna, K. R. et al. (1981) Protoplasma 107:319–337.
Dickinson, H. G. et al. (1982), Proc. R. Soc. B 215:45–62.
Williams, E. G. et al, (1982), Planta 156:517–519.
Harris, P. J. et al, (1984), Oxford Surveys Plant Molec. Cell Biol. 1:161–203.
Rae, A. L. et al. (1985), Planta 166:128–133.
Anderson, M. A. et al. (1984), Plant Physiol. 75:1013–1016.

*Primary Examiner*—Robert J. Warden
*Assistant Examiner*—Richard Wagner
*Attorney, Agent, or Firm*—Greenlee and Associates

[57] ABSTRACT

This invention provides an immunologic method for measuring plant pollen germination and pollen tube growth. This method is based on the finding that an antibody having specificity to $\beta$-L-arabinofuranosyl residues binds to the surface of in vitro grown pollen tubes. Antibody binding can be measured qualitatively or quantitatively using a calibration curve. The immunoassay is useful for screening plants for response to substances that affect plant germination or pollen tube growth.

9 Claims, 1 Drawing Sheet

POLLEN TUBE GROWTH ASSAY

INTRODUCTION AND BACKGROUND

The present invention lies in the field of immunoassays, specifically providing an immunoassay for quantitative and qualitative measurement of plant pollen tube growth.

The measurement of in-vitro pollen germination and pollen tube growth has been shown to be a sensitive means for measuring the response of plant tissue to a variety of chemical and environmental stresses. For example, the measurement of pollen tube growth has been used to select plants for resistance to herbicides and heavy metal ions. See, for example, Smith, G.A. and Moser, H.S. (1985) Theor. Appl. Genet. 71:231; Feder, W.A. (1986) in *Biotechnology and Ecology of Pollen*, D.L. Mulcahy, G. V. Mulcahy, E. Ottaviano (Eds.). Springer-Verlag, New York, p. 89; Searcy, K.B. and Mulcahy, D.L. (1985) Amer. J. Bot. 72:1700; Searcy, K.B. and Mulcahy, D.L. (1986) in *Biotechnology and Ecology of Pollen (supra.)* p 159. The bioassay of pollen tube growth has also been used to investigate the effects on pollen growth of style extracts and glycoproteins associated with self-incompatibility. See Shivanna, K.R. et al. (1981) Protoplasma 107:319; Dickinson, H.G. et al. (1982) Proc. R. Soc. B 215:45; Williams, E.G. et al. (1982) Planta 156:517.

The growth of pollen in-vitro has usually been determined directly, counting the percentage of grains that germinate and measuring pollen tube length by direct measurement. Such methods are tedious, time consuming and wholly unsuited for large samples or for automation. Furthermore, measurements of pollen tube length, whether made using a microscope fitted with an eye piece graticule or a semi-automated image analysis system are, to a certain extent subjective. The present invention provides a new method for measuring pollen tube growth based upon an immunoassay which has been discovered to provide a quantitative measurement of growth.

Chemical studies of the cell wall composition of pollen tubes have been reviewed by Harris, P.J. et al. (1984) Oxford Surveys Plant Molec. and Cell Biol. 1:161–203. Such studies have included the monocotyledons, Lilium, and Tulipa as well as the dicotyledons, Camellia, Petunia, and Nicotiana. Most of the prior studies have been confined to analyses of monosaccharides in acid hydrolysates of whole cell walls or cell wall fractions. The composition of the pollen cell walls of *Nicotiana alata* have been found to consist primarily of callose, a (1>3)-$\beta$-D-glucan and a (1>5)-$\alpha$-L-Arabinan as primary components, together with small amounts of cellulose and a uronic acid-containing polysaccharide localized at the pollen tube tip. Rae, A.L. et al. (1985) Planta 166:128.

Although it is sometimes difficult to generate an antibody response to polysaccharides, especially those of animal origin, it is sometimes observed that polysaccharides of plant origin do generate an antibody response. Anderson, M.A. et al. (1984) Plant Physiol. 75:1013, have shown that mice can be immunized with extracts of the styles of mature flowers of *Nicotiana alata*. The authors reported that about half the hybridomas derived from such an immunization secreted antibodies to *N. alata* style arabinogalactan protein (AGP). The AGP of *N. alatastyles* contains 68% carbohydrate of which arabinose and galactose are the major components. Furthermore, a high proportion of the hybridomas were directed to both L-arabinose and D-galactose, since antibody binding to the isolated AGP was inhibited by either L-arabinose or D-galactose, but not by glucose. Other hybridomas were produced which secreted antibody with preference for L-arabinose compared with D-galactose, or with preference for D-galactose compared with L-arabinose. It was found in the studies that a monoclonal antibody could be selected which had preferential binding for L-arabinose residues and that polysaccharides with a single terminal arabinofuranosyl residue were also bound by the antibody. Harris et al. (1984) disclosed that an o-L-arabinofuranosyl directed monoclonal antibody also bound to the surface of in-vitro grown *N. alata* pollen tubes.

Antibodies, both polyclonal and monoclonal, are wellknown in the art. Given source materials specified as to composition or method of preparation to be used as antigens, a variety of techniques of immunization, purification and selection are well-known in the art for producing polyclonal and monoclonal antibodies. Techniques for preparing monoclonal antibodies (MABs) were initially described by Kohler, G. and Milstein, C. (1975) Nature 256: 495, and more recent publications on the subject include Reuveney, S. et al. (1985) Develop. Biol. Standard 60:185; Bodeus, N. et al. (1985) J. Immunol. Meth. 79:1; and *The Commercial Production of Monoclonal Antibodies*, S. Seaver (Ed.) Marcel Dekker, Inc., New York (1986). The method used for preparing the monoclonal antibody exemplified herein was described by Anderson, M.A. (1984), supra.

Immunoassay techniques have also been described in great detail in publications over the last 10 to 15 years. Enzyme-linked immunoassays (ELISA) have been described for example by Engvall, E. in Methods in Enzymology 70:419.

SUMMARY OF THE INVENTION

The invention provides a quantitative and qualitative immunoassay for pollen germination and pollen tube growth in solanaceous plants. Important aspects in the development of the assay were the discovery that antibodies directed to L-arabinofuranosyl residues bind to germinating pollen and growing pollen tubes, but not to pollen grains, in a manner which bears a quantitative relationship to pollen tube length. The assay may be developed using polyclonal or monoclonal antibodies, as long as the antibodies are specific to a structural pollen tube component, preferably one located on the pollen tube outer surface, most preferably one which carries exposed $\alpha$-L-arabinofuranosyl residues. MABs are preferred because of their greater binding specificity and lower background of nonspecific binding. Any technique for quantitatively measuring antibody binding, including but not limited to enzyme linked immunoassay (ELISA), radioimmunoassay (RIA) or fluorescent-labeled anti-immunoglobulin binding assay can be employed. The assay is useful for measuring pollen viability, screening for resistance to inhibitors including herbicides or other phytotoxic substances, and for quantitatively measuring the activity of inhibitors such as herbicides, gametocides, toxins, self-incompatibility proteins, and the like. The assay may also be used to measure the effects of growth enhancers such as hormones, and antagonists of inhibitors, such as safeners and plant protectants. An example of the method is described in detail, wherein a monoclonal antibody derived by immunization with style AGP is employed and antibody binding to pollen tubes measured by an ELISA assay. The described assay is exemplary only, as the method of the invention may be practiced with any polyclonal antibody or MAB directed to and specific for a pollen tube structural component preferably one located on the pollen tube outer surface, and most preferably one which carries exposed α-L-arabinofuranosyl residues. The method may be practiced using any immunoassay capable of measuring the binding of the antibody to pollen. It will be understood by those of ordinary skill in the immunoassay art that sufficient binding affinity, specificity for the target α-L-arabinofuranosyl groups and sensitivity in the assay method must be present to devise a workable assay within the scope of the invention, however, these parameters will be readily understood and readily measurable without undue experimentation following the state of the art and the teachings herein. Specific reaction conditions such as temperature, pH, buffer composition, etc. may be varied as understood by those of ordinary skill in the art, as long as the conditions chosen are suitable for antigen-antibody binding and for the measurement reactions to occur.

The assay in its general form may be applied to any pollen-producing plant species where pollen can be germinated in-vitro. Pollen tube structures show great similarity among both monocots and dicots. The MAB exemplified herein can be used for assaying pollen tube growth of any solanaceous plant, and will be useful also in any species where α-L-arabinofuranosyl groups are exposed on the pollen tube surface. Other antibodies, having broader or narrower specificity can be developed, for use in measuring pollen growth of any pollen-producing plant.

Although pollen tube growth may be linear with time (see Fig. 1A) the distribution of antibody binding sites may not be uniform along the tube. Quantitative analysis of mean pollen tube length will, in many instances, depend upon constructing a calibration curve to correlate amount of antibody bound with mean pollen tube length, as determined by an independent (or previously calibrated) assay. The calibration must be carried out under the same experimental conditions as the assay itself. A calibration curve should be constructed whenever the assay is applied to a different plant species, or where the antibody or method of measurement are changed. The calibration need not be carried out by direct observation if a previously calibrated assay is available.

BRIEF DESCRIPTION OF THE DRAWING

FIG. 1 shows experimental data correlating pollen tube length as measured by direct observation with time of germination and color development in the exemplified ELISA assay.

DETAILED DESCRIPTION OF THE INVENTION

Figure 1A:
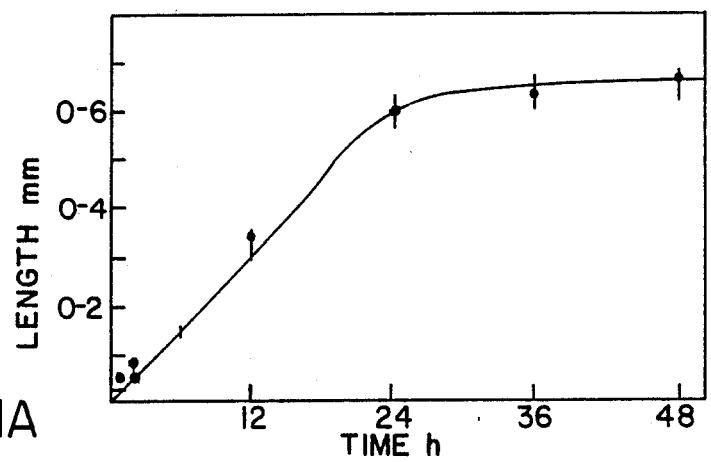
FIG. 1A is a plot of mean pollen tube length as a function of time of germination.

The following description includes the use of abbreviations, which if not otherwise specified, are standard in the art and commonly used in professional journals such as those cited herein. The monoclonal antibody used in this example, designated PCBC3, was derived from a mouse immunized with a style extract of *Nicotiana alata*, as described by Anderson, M.A. et al. (1984) supra. The antibody has been purified from the hybridoma supernatent by affinity chromatography on a protein A-sepharose column and is available commercially from Biosupplies Australia, P.O. Box 835, Parkville, Victoria 3052. The protein concentration was 0.27 mg/ml and it was used in the ELISA at a dilution of 1:20. Since the MAB was not derived using a pollen tube component as an antigen, the ability of the antibody to bond pollen tubes is due to a structural component common to both AGP, the immunizing antigen, and pollen tube walls. The common component is α-L-arabinose, which is present in many polysaccharides and glycoproteins, including AGP. The MAB in this instance recognizes and binds specifically to α-L-arabinofuranosyl groups on a variety of polymeric structures and the binding is inhibited by α-L-arabinose itself. Therefore, any antibody which specifically bonds α-L-arabinofuranosyl groups will function in the method of the invention and such antibodies may be derived by immunization with many polysaccharides and glycoproteins that contain such groups. As a control antibody, nonspecific for pollen tubes, a monoclonal antibody designated K32F2 against hepatitis A virus was used (Macgregor, A. et al. (1983) J. Clin. Microbiol. 18:1237). *Nicotiana alata* is an ornamental species that is widely available. In these experiments seeds of *Nicotiana alata* Link et Otto (self-incompatibility genotype S2S3) were provided by Dr. K. K. Pandey, Division of Industrial and Scientific Research, Grasslands Division, Palmerston North, New Zealand. Plants were grown individually in greenhouse pots. Mature pollen of *N. alata* was collected, mixed and samples of 10 mg each stored in small plastic tubes, sealed and kept in liquid nitrogen.

For germination, pollen was removed from storage in liquid nitrogen and thawed quickly by placing the tube in water at 37° C. for one minute. The open tube was then placed in a sealed container, saturated with water vapor for 30 minutes at 23° C. Pollen was then dispersed in germination medium in a pre-sterilized tube by agitation on a vortex mixer. Germination medium contained 0.3 M sucrose, 1.3 mM $Ca(NO_3)_2$, 0.81 mM $MgSO_4$, 1.0 mM $KNO_3$, 1.6 mM $H_3BO_3$, 5 μg/ml rifampicin and 7.5 μg/ml nystatin. The medium was sterilized by filtration using a Pre-sterilized disposable filter (0.2 μm pore size) in a polycarbonate filter holder (Schleicher and Schuell, Dassal, West Germany).

Aliquots (200 μl) of the pollen suspension were pipetted into the wells of a filter microtiter plate (0.2 μm pore size) (Millititer GV filtration plate, Millipore Corporation). The pollen suspension was mixed between each transfer. The lid was placed on the plate which was then placed in a plastic tray containing a strip of filter paper (Whatman No. 1) moistened with water to maintain a high relative humidity. The tray was shaken (100 rpm) on an orbital shaker (model PO 1412, Paton Industries, South Australia) at 23° C. in the dark for up to 48 hours. The outer wells of the filter microtiter plate were not used due to poor pollen growth in these wells. The ELISA was done on germinated pollen immediately or, if this was inconvenient, after storage at 4° C. for no longer than 48 hours. Aliquots (200 μl) of the same pollen suspension were pipetted into the wells of a second filter microtiter plate and stored at −20° C. This permitted the amount of monoclonal antibody that binds to ungerminated pollen to be measured.

All transfers were done in a laminar flow hood. Pipette tips (200 μl) capacity) were sterilized by autoclaving (121° C., 106 kPa, 30 min.) and the lid and plastic tray were disinfected by wiping with 70% v/v ethanol. Unused filter microtiter plates were sterile, but after using some of the wells, the whole plate was sterilized so that the remaining wells could be used. This was done by rinsing the plate with water (5 times) and sterile water (sterilized by autoclaving) (3 times), then exposing the plate to UV radiation in the laminar flow hood for 10 minutes. Possible contamination of germinated pollen cultures was tested for by plating aliquots (30 μl) onto peptone-glucose agar. The plates were incubated at 37° C. and 23° C. for 48 hours and then examined for bacterial and fungal colonies. The culture medium was also examined for contamination by bright-field microscopy. Contamination was not detected by either means.

ELISA on pollen.

Ungerminated pollen (stored at −20° C.), or germinated pollen in the wells of filter microtiter plates, was washed (3 times) with Tween 20 (TM ICI Americas Inc., Wilmington, DE, USA) (0.5% v/v) in PBS (0.02 M sodium phosphate buffer (pH 7.5) containing 0.15 M NaCl (PBS-Tween). PBS-Tween was used for all washing steps in the assay. Nonspecific binding sites on the pollen and the wells were blocked by incubation with BSA (2% w/v; Fraction V, Sigma Chemical Co.) in PBS (PBS/BSA) (200 μl) at 23° C. for 2 hours. The PBS/BSA was removed and monoclonal antibody (primary antibody) (100 μl) (diluted 1:20) in PBS/BSA added and incubated for 2 hours at 37° C. After washing (5 times), anti-mouse Ig(Fab')$_2$ fragment (from sheep) labeled with β-galactosidase (from *Escherichia coli*) (secondary antibody) (Amersham International, Amersham, UK) (75 μl) (diluted 1:50) in PBS containing ovalbumin (2% w/v; Grade V, Sigma Chemical Co.), 10 mM MgCl$_2$, 1 mM 2-mercaptoethanol, and Tween 20 (0.5%, v/v) was added and incubated for 2 hours at 37° C. After washing (7 times), the substrate, O-nitrophenyl-β-D-galactopyranoside (150 μl) (0.9 mg/ml in PBS containing 10 mM MgCl$_2$ and 0.1 M mercaptoethanol was added and incubated for 40 minutes at 37° C. An aliquot (100 μl) was removed from each well and transferred to the wells of a conventional microtiter plate (Costar, Cambridge, UK) and 1 M Na$_2$CO$_3$ (50 μl) added to bring the pH to ≧10 and stop the reaction. The O-nitrophenol released was determined by measuring the absorbance at 414 nm using a multichannel colorimeter connected to a Titertek Multiscan MC (Flow Laboratories, McLean, VA.). The rate of release of O-nitrophenol was linear for at least 40 minutes in all experiments reported. Controls were set up using no primary antibody and no primary or secondary antibody. A further control was included in which a monoclonal antibody raised against hepatitis A virus (at the same protein concentration as PCBC3) was used to check for nonspecific binding.

The effect of L-arabinose (BDH, Poole, UK) and the disaccharide, 3-O-β-D-galactopyranosyl-D-arabinose (Gal-1-3-Ara)(Sigma Chemical Co., St. Louis, MO USA) on the binding of the monoclonal antibody (PCBC3) to pollen, germinated for 48 hours, was determined by ELISA in the presence of these sugars using antibody preincubated with these sugars (2 hours at 23° C.).

Treatment of germinated and ungerminated pollen with sodium metaperiodate almost completely prevented binding of the monoclonal antibody (PCBC3).

Measurement of Pollen Tube Length and Percentage Germination.

After completion of the ELISA, germinated pollen in the wells of the filter microtiter plate was resuspended in PBS (150 μl). Aliquots (30 μl) of this suspension were transferred to a microscope slide, mixed with formaldehyde (4% v/v) in PBS (20 μl), covered with a coverslip (22×50 mm), and sealed with nail polish. The suspension was transferred from the wells using an automatic pipette fitted with a 200 μl capacity tip, the distal 2.5 cm of which was cut off. This prevented breakage of pollen tubes longer than approximately 500 μm. The lengths of 50 pollen tubes from each well were measured using a Videoplan computerized image analysis system (Zeiss, Oberkochen, FRG). The percentage germination was determined by examining 100 pollen grains from each well.

Initial ELISAs were done on pollen germinated for 48 hours. The results showed that the monoclonal antibody (PCBC3), which has a primary specificity for α-L-arabinofuranosyl residues, bound to germinated pollen, but showed little or no binding to ungerminated pollen grains. There was a low level of nonspecific binding of the secondary antibody to both germinated and ungerminated pollen. The low absorbances obtained when neither the primary nor the secondary antibody was used indicate that the endogenous β-galactosidase activity at pH7.5 in germinated and ungerminated pollen was low. Only a small amount of the monoclonal antibody (K32F2), raised against hepatitis A virus, bound to germinated or ungerminated pollen.

Figure 1B:
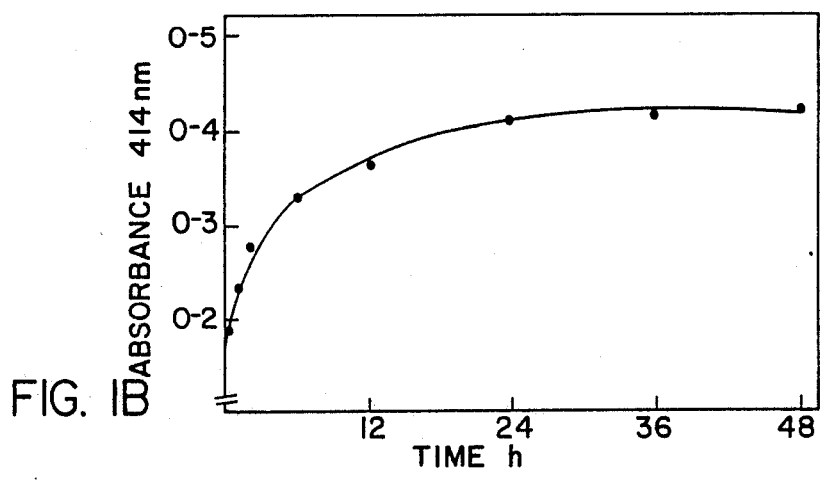
FIG. 1B is a plot of binding of anti-α-L-arabinofuranosyl antibody, determined by ELISA, to pollen tubes as a function of time after germination.
Figure 1C:
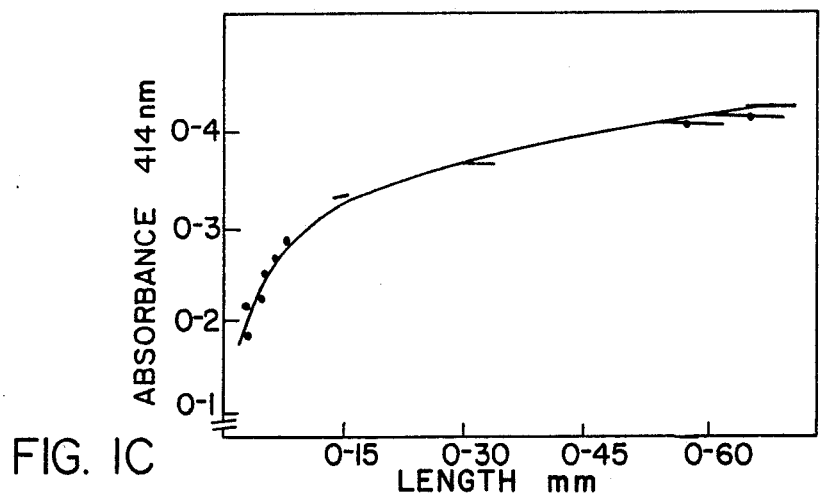
FIG. 1C is a plot of the relationship between binding of the anti-α-L-arabinofuranosyl antibody determined by ELISA (absorbance 414 nm) and mean length of pollen tubes.

The pollen tubes grew at an average rate of approximately 26 μm/h for 24 hours, after which the growth rate was much slower (FIG. 1A). ELISAs on pollen germinated for up to 48 hours showed that there was a considerable amount of binding of the anti-arabinosyl monoclonal antibody after only 30 minutes of germination (FIG. 1B); and that the binding continued nonlinearly up to a maximum on pollen tubes germinated for 24 hours. FIG. 1C shows the relationship between pollen tube length and absorbance (at 414 nm) obtained using the ELISA. Most data points fit a logarithmic relationship obtained using linear regression analysis by the method of least squares. The regression equation is: absorbance =0.448+0.0688 length.

L-arabinose and 3-O-β-D-galactopyranosyl-D-arabinose inhibited the binding of the monoclonal antibody (PCBC3) to germinated pollen. The disaccharide was a more effective inhibitor than L-arabinose.

Treatment of germinated and ungerminated pollen with sodium metaperiodate almost completely prevented binding of the monoclonal antibody (PCBC3).

Both 2-deoxy-D-glucose and nonanoic acid reduced percentage germination and pollen tube growth.

The results plainly demonstrate that the MAB PCBC3 binds to pollen tubes of *N. alata* grown in vitro, and that the quantity of binding increases with increasing pollen tube length. If the antibody bound evenly over the whole length of the pollen tube, and if the diameter of the pollen tube remained constant, the amount of antibody bound would be directly proportional to the surface area and hence, to the length. However, as shown in FIG. 1, the relationship between amount of antibody bound and mean tube length was not linear, but approximately logarithmic. More antibody was bound per unit length for short tubes than for long tubes. An initial calibration of the assay is therefore required in order to establish the quantitative relation between absorbance (amount of antibody bound) and pollen tube length. Therefore, if a different antibody were to be used in the assay, it is possible that the quantitative relationship between amount of antibody bound and pollen tube growth would vary somewhat and a fresh calibration would be recommended. Since the short tubes and newly germinated pollen contribute more heavily to the total absorbance in the ELISA assay, a single measurement of absorbance at a given time after germination will be affected by the pollen viability, or the percent of pollen grains that germinate. However, it has been observed that most inhibitors of pollen tube growth are also inhibitors of germination as is the case, for example, with 2-deoxy-D-glucose and nonanoic acid. Therefore, the utility of the assay for screening inhibitory compounds will not be seriously affected. It will be understood that it is possible to control for variations in percentage germination by direct observation and also to add the inhibitor after germination has initiated. In any event, the ELISA method allows large numbers of substances at different concentrations to be screened for their effects on overall pollen growth, i.e., combined germination and tube growth.

A method for screening plants for resistance to substances that affect pollen tube growth therefore follows from the principles of the assay. Pollen of individual plants is collected, separated into samples and some samples are allowed to germinate in-vitro, some in the presence of the inhibitor and some in its absence. Growth of the pollen tubes in the presence and absence of inhibitor is measured by the described assay method. Preferably, a range of inhibitor concentrations is used to measure the dose response and calculate sublethal doses suitable for screening. Pollen which displays resistance to the inhibitor is then used to fertilize female plants to initiate a new round of selection. Effects of the inhibitor on germination and tube growth can be separated by measuring antibody binding shortly after germination has been initiated and by allowing germination to occur in the absence of inhibitor, then measuring subsequent tube growth in the presence of inhibitor.

The inhibitory effects of L-arabinose, 3-O-$\beta$-D-galactopyranosyl-D-arabinose and sodium metaperiodate on the antibody binding indicate that the observed increases in absorbance are in fact due to specific antibody binding to carbohydrate. It will be understood that studies of suspected growth inhibitors must be controlled for possible effects on the assay itself, either as an effect on antigen-antibody binding or on the measurement reaction.

Immunofluorescence microscopy was carried out using Texas Red labeled anti-immunoglobulin, in order to visualize the areas of strongest antibody binding to the pollen tube. The results revealed that pollen germinated for only 30 minutes had a strongly fluorescent cap at the end of a short tube. Tubes of pollen germinated for 6 hours showed a weaker fluorescence along the length of the tube; in some tubes the fluorescence was brighter at the tip or immediately behind the tip. The fluorescence became progressively weaker farther back along the tube. The strongly fluorescent cap, detected using immunofluorescent microscopy, at the end of pollen tubes germinated for only 30 minutes, probably accounts for the considerable amount of binding of the monoclonal antibody measured using the ELISA after only 30 minutes germination. At present, the composition of the cap is not known, nor is it known what structures bind the antibody. However, it is known that an L-arabinan is a major component of the cell walls of N.-alata pollen tubes. The arabinan has terminal $\alpha$-L-arabinosyl residues and is located preferentially in the outer wall layer of the pollen tube.

Pollen tubes of a wild tomato, like Lycopersicon peruvianum, another member of the Solanaceae, grown invitro, bind the same anti-arabinosyl antibody similarly to N. alata. Therefore, the assay herein exemplified, with antibody PCBC3, is applicable to members of the Solanaceae. However, it will be apparent to those of ordinary skill in the art that other monoclonal antibodies against pollen tube walls can be selected which will then be useful in an ELISA assay for measuring the growth of pollen tubes in other species of plants.

We claim:

1. A method for qualitative or quantitative measurement of in-vitro pollen germination and pollen tube growth comprising:
    (a) incubating pollen at a desired germination stage with an antibody specific for a pollen tube structural component,
    (b) measuring the amount of said antibody bound to said pollen, and
    (c) relating said amount of bound antibody to pollen germination and to an amount of pollen tube growth according to a calibration curve comparing pollen tube length with amount of antibody bound under the same test conditions.

2. The method of claim 1 wherein the antibody is specific for $\alpha$-L-arabinofuranosyl groups.

3. The method of claim 1 wherein the antibody is a monoclonal antibody.

4. The method of claim 1 wherein the antibody is a monoclonal antibody directed to style arabinogalactan protein (AGP).

5. The method of claim 1 wherein the antibody is the monoclonal antibody PCBC3.

6. The method of claim 1 wherein an ELISA assay is used in the step of measuring the amount of antibody bound.

7. The method of claim 1 wherein a radioimmunoassay is used in the step of measuring the amount of antibody bound.

8. The method of claim 1 wherein immunofluorescence is used to measure the amount of antibody bound.

9. A method of screening plants for response to a substance that affects pollen germination and pollen tube growth comprising:
    (a) exposing a first aliquot of pollen at a desired germination stage to said substance under pollen germination conditions,
    incubating a second aliquot of said pollen under said pollen germinating conditions in the absence of said substance,
    (c) incubating said first and second aliquots of pollen with an antibody specific for a pollen tube structural component,
    (d) measuring the amount of said antibody bound to said pollen, (e) relating said amount of bound antibody to pollen germination and to an amount of pollen tube growth according to a calibration curve comparing pollen tube length with amount of antibody bound under the same test conditions, and
(f) comparing pollen germination and pollen tube growth rates in the presence and absence of said substance whereby the response of plants to a substance that affects pollen tube growth is screened.

* * * * *